United States Patent [19]

Beacham

[11] Patent Number: 5,086,766
[45] Date of Patent: Feb. 11, 1992

[54] MEDICAL BREATHING APPARATUS

[75] Inventor: Allan Beacham, Andover, United Kingdom

[73] Assignee: Virotherm Laboratories Ltd., United Kingdom

[21] Appl. No.: 585,068

[22] PCT Filed: Apr. 6, 1989

[86] PCT No.: PCT/GB89/00357
§ 371 Date: Oct. 15, 1990
§ 102(e) Date: Oct. 15, 1990

[87] PCT Pub. No.: WO89/09632
PCT Pub. Date: Oct. 19, 1989

[30] Foreign Application Priority Data
Apr. 16, 1988 [GB] United Kingdom ............... 8809039

[51] Int. Cl.⁵ ............................................. A61M 16/00
[52] U.S. Cl. ........................ 128/203.27; 128/203.26; 128/203.17; 128/204.17
[58] Field of Search ................ 128/203.16, 203.17, 128/203.26, 203.27, 204.17

[56] References Cited

U.S. PATENT DOCUMENTS

| | | | |
|---|---|---|---|
| 1,858,580 | 5/1932 | Collins | 128/203.17 |
| 1,998,327 | 4/1935 | McGuire | 128/203.27 |
| 3,152,240 | 10/1964 | Scott | 128/203.27 |
| 3,518,409 | 6/1970 | Corbett | 128/203.17 |
| 3,579,262 | 5/1971 | Peeps | 128/203.19 |
| 3,894,537 | 7/1975 | Camp | 128/203.17 |
| 3,949,743 | 4/1976 | Shanbrom | 128/200.14 |
| 4,604,999 | 8/1986 | Maeda | 128/203.17 |
| 4,637,387 | 1/1987 | Hall | 128/205.24 |
| 4,676,237 | 6/1987 | Wood et al. | 61/285 |
| 4,942,874 | 7/1990 | Terada et al. | 128/203.26 |

FOREIGN PATENT DOCUMENTS

| | | |
|---|---|---|
| 0190080 | 1/1986 | European Pat. Off. . |
| WO8500525 | 8/1984 | Fed. Rep. of Germany ............ 128/203.17 |
| 3707659 | 9/1988 | Fed. Rep. of Germany ............ 128/203.26 |
| 80095 | 1/1963 | France ........................ 128/203.27 |
| 0125210 | 5/1984 | France . |
| 0175630 | 9/1985 | France . |
| 381388 | 10/1932 | United Kingdom ......... 128/208.27 |
| 1294808 | 11/1972 | United Kingdom . |
| 2192136 | 7/1987 | United Kingdom . |

Primary Examiner—Edgar S. Burr
Assistant Examiner—Lisa Malvaso
Attorney, Agent, or Firm—Davis, Bujold & Streck

[57] ABSTRACT

A breathing apparatus of the kind having a water chamber in which a heating element is immersed, the temperature of said element being controlled so that air drawn over the heated water is maintained at or close to a required humidity and temperature at an outlet, the volume of the air passing through the apparatus being substantially greater than that required for breathing and being directed into a face mask connectable to the outlet which is formed with vents through which excess moist/heated air together with air exhaled by a user can pass to atmosphere, is characterized in that the casing for the apparatus is in two parts, comprising a base and a removable housing, in that the base accommodates a water tank, and has a column extending upwards therefrom which defines an air path from the water tank in that the face mask is connected to the upper, outlet end of the column, and in that the heating element is carried by and projects from said removable housing such that it is immersed into the water of said tank when said housing is fitted into position on said base.

6 Claims, 3 Drawing Sheets

MEDICAL BREATHING APPARATUS

This invention relates to breathing apparatus for medical purposes.

It is known that humid air at around 90% relative humidity and a critical temperature of 43° C., when breathed by a patient for period of 15 to 20 minutes, is effective in rendering groups of viruses in the upper respiratory tract inactive, which results in the body being able to counteract colds, allergies, etc. efficiently and thereby reduce dramatically the patient's recovery time.

The Applicant's co-pending U.K. Patent Specification No. 2192136, describes apparatus which incorporates an efficient temperature control arrangement by which air drawn through the apparatus is supplied to the user at or close to the critical humidity and temperature requirements. This apparatus has proved particularly successful in clinical trials conducted by the Medical Research Council.

The object of the present invention is to provide a development of the apparatus described in our said co-pending Patent Specification which, compared with the various embodiments described therein, has further mainly constructional, advantages.

According to this invention breathing apparatus of the kind having a water chamber in which a heating element is immersed, the the temperature of said element being controlled so that air drawn over the heated water is maintained at or close to a required humidity and temperature at an outlet, the volume of the air passing through the apparatus being substantially greater than that required for breathing and being directed into a face mask connectable to the outlet which is formed with vents through which excess moist/heated air together with air exhaled by the user can pass to atmosphere, is characterised in that the casing for the apparatus is in two parts, comprising a base and a removable housing, in that the base accommodates a water tank and has a column extending upwards therefrom which defines an air path from the water tank, in that the face mask is connected to the upper, outlet end of the column, and in that the heating element is carried by and projects from said removable housing such that it is immersed into the water of said tank when said housing is fitted into position on said base.

Preferably, the heating element is of the PTC (Positive Temperature Co-efficient) type and is surrounded by a shroud, which may be detachable, and which generally encloses said element, but provides openings near the top of the shroud, the arrangemen being such that, when the apparatus is not in use the heating element cannot be touched if the removable housing is removed, and when the apparatus is in use water at the required temperature tends to be concentrated within the shroud and across the water surface, thereby providing a reduced thermal mass and a consequent improvement in temperature control.

The base and removable housing may be so shaped that, when fitted together, they provide a casing which tapers progressively to a small dimension in plan from its lower to its upper end, thereby providing stability to the apparatus in use, in which case a frontal part of the apparatus projects upwardly from the base and is inclined to the vertical away from the user, said frontal part preferably comprises front and side walls which are generally of U-cross-section, and the side walls thereof co-operate when fitted with a similarly inclined front wall of said removable housing to define said column. The removable housing may conveniently accommodate all the electrical/electronic components for the apparatus, which includes a fan and fan motor, said heating element, and a circuit arrangement therefor. The circuit arrangement may include provision for temperature control including a temperature sensor for monitoring the temperature of the moist/heated air being inhaled, which is fitted in the removable housing so as to project into said column at or close to its outlet.

Conveniently, the water tank is removable from the base for easy filling and cleaning.

In order that the invention may be readily understood, one embodiment of breathing apparatus in accordance therewith will now be described, by way of example, with reference to the accompanying drawings, in which.

Figure 1:
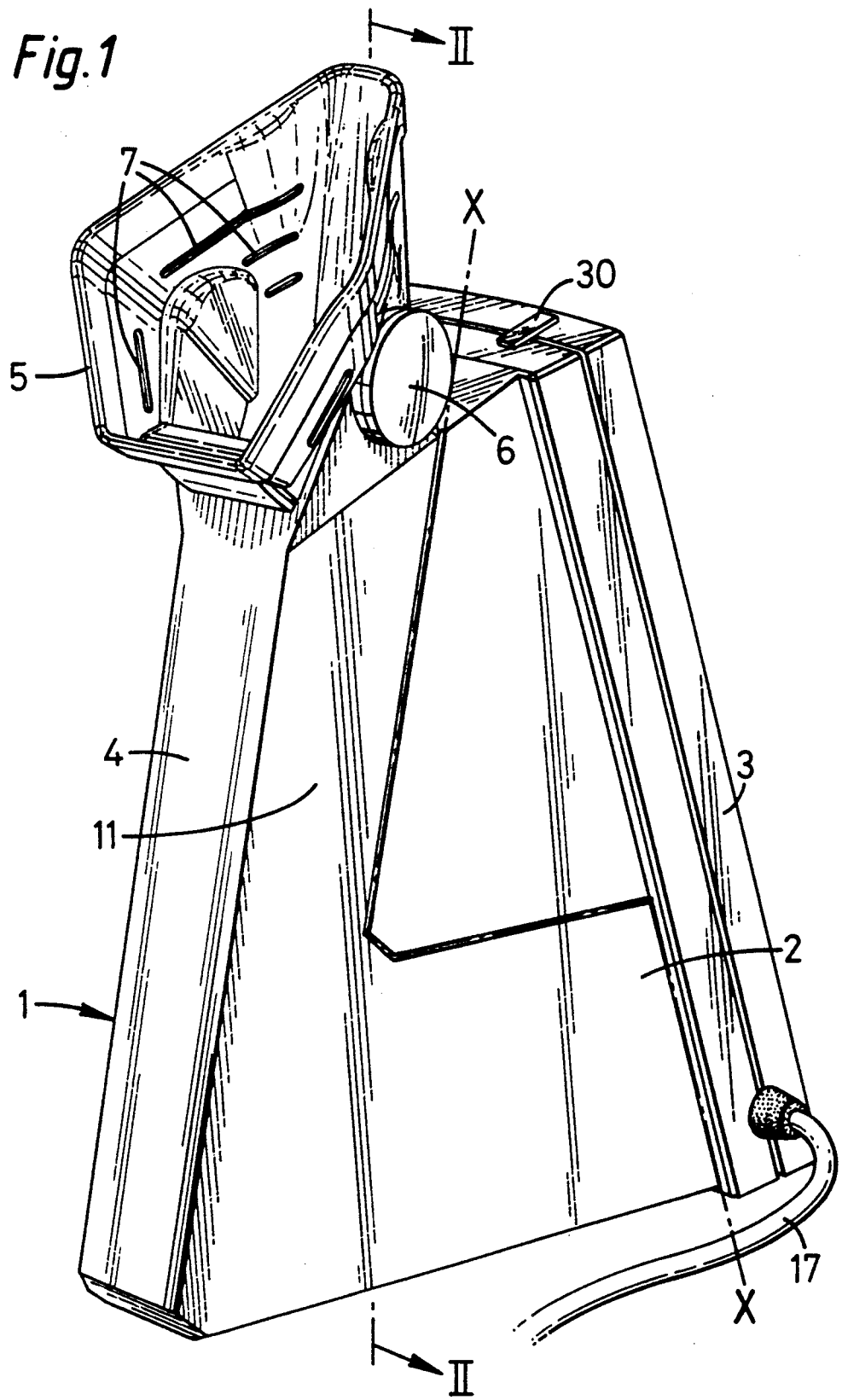
FIG. 1 is a perspective view of the apparatus.
Figure 2:
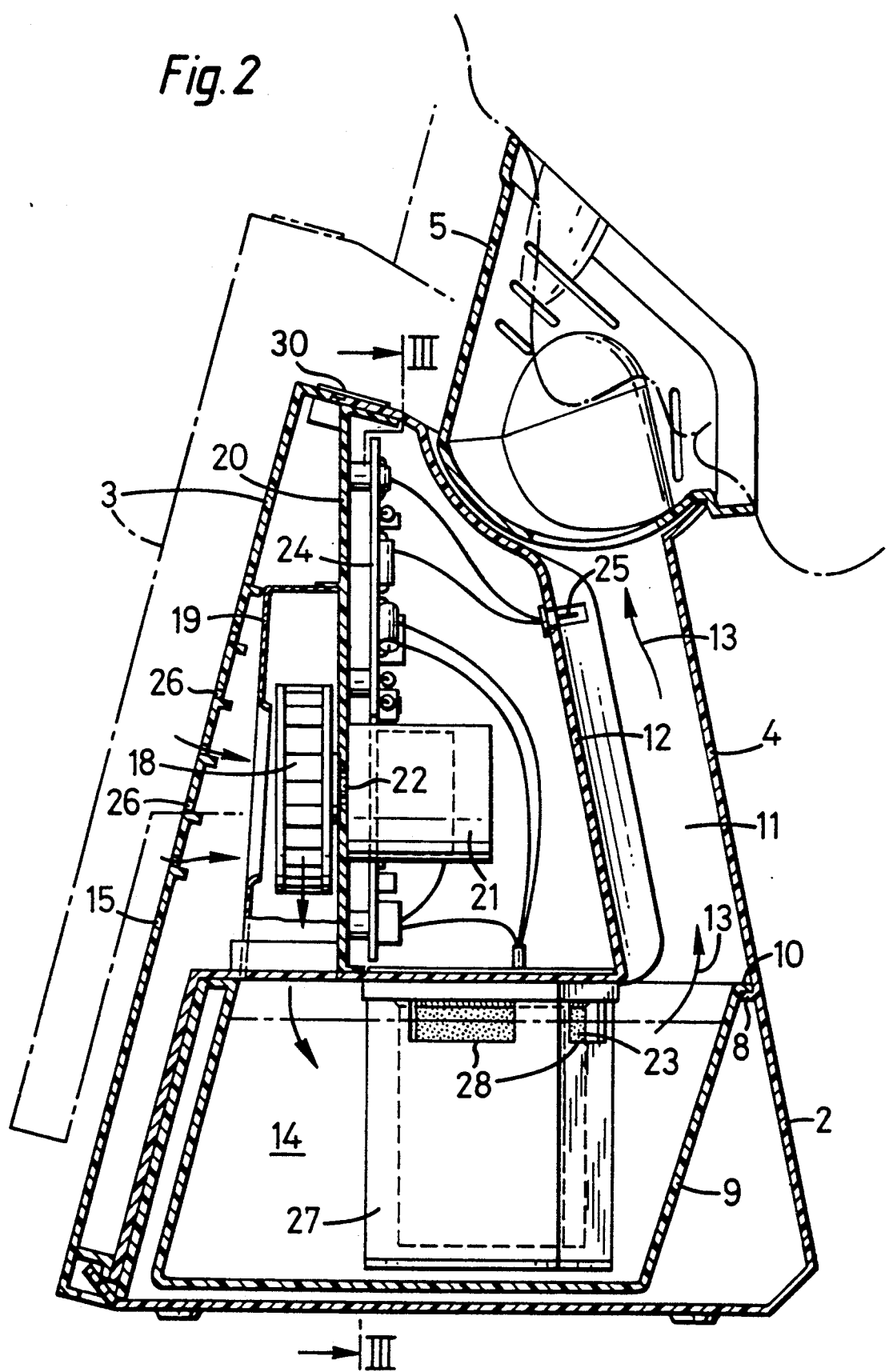
FIG. 2 is a cross-sectional side view, on the line II—II of FIG. 1.

Referring to FIG. 1, it will be seen that the casing 1 is generally in two parts consisting of a base 2 and a removable housing 3, the split line being along the thickened line X—X (see also the chain dotted outline of the housing 3 in FIG. 2). The front wall of the base (i.e. the wall facing the user) includes a column 4 which projects upwardly, but is inclined to the vertical away from the user. The upper end of the column supports a face mask 5 via pivoted mountings 6, said face mask being provided with a series of slit openings 7, as described in our said co-pending Patent Specifiction No. 2192136.

Figure 3:
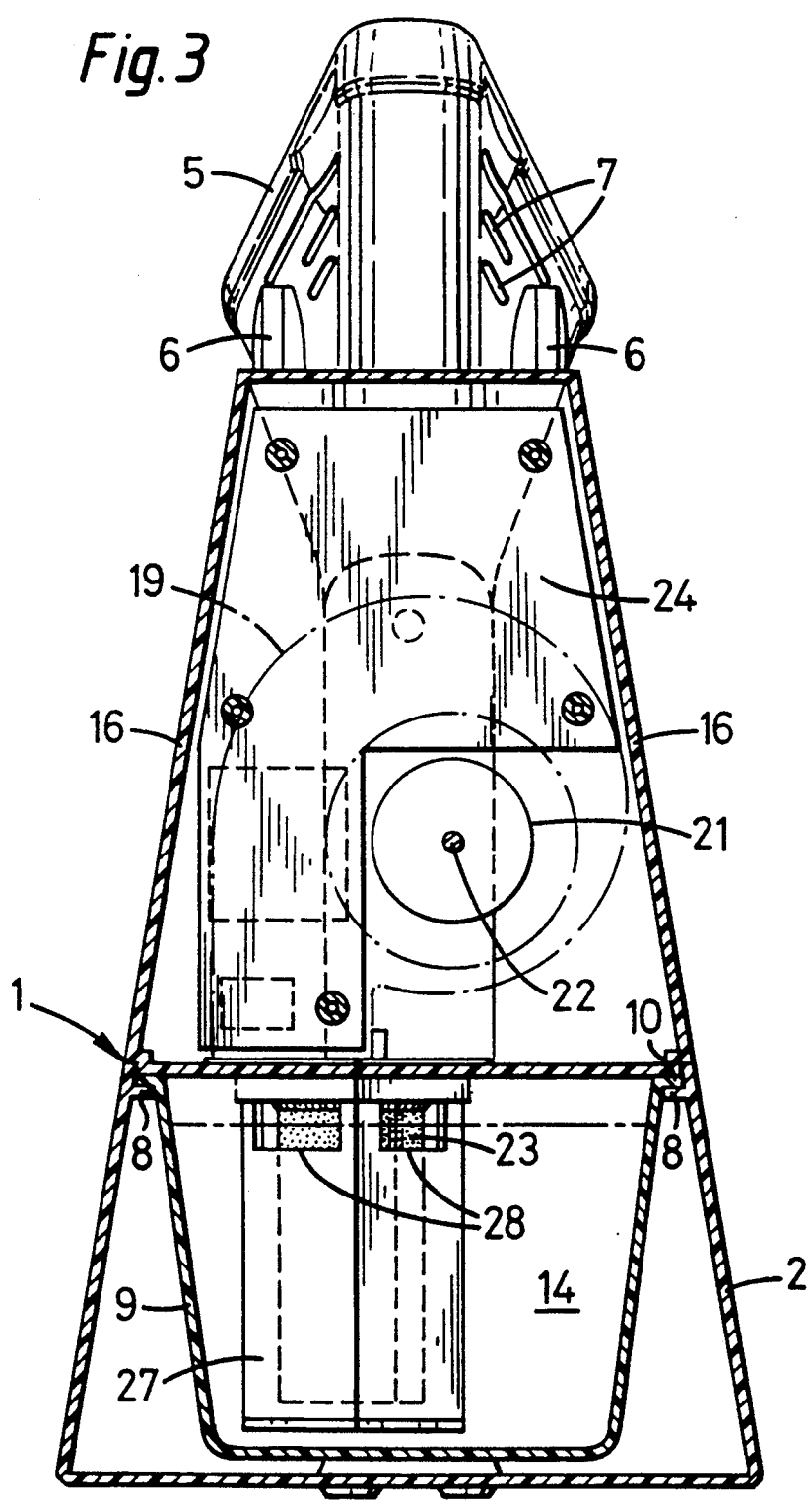
FIG. 3 is a section on the line III—III of FIG. 2.

Referring to FIG. 2, the base 2 has a continuous horizontal ledge 8 extending around its front and side walls (see also FIG. 3) which support an open water tank 9, via a flange 10 extending around the top of said tank. The inclined column 4 is generally of U-cross section and the side walls 11 thereof (see also FIG. 1) co-operate (when fitted) with a similarly inclined front wall 12 of the removable housing 3 to define a path, denoted by arrows 13, above the tank 9, for the flow (in use) of moitst/heated air passed across the surface of water 14 contained in the tank, to the face mask 5.

The removable housing 3 accommodates all the electrical/electonic components for the apparatus, which are fed from a suitable power supply via an electric cable 17, (see FIG. 1). The components include a fan 18, which is rotatable within a volute casing 19 mounted on one (rearward facing) face of a support wall 20 extending vertically within the housing 3, a fan motor 21 supported on the other face of the wall 20 which is coupled to the fan via a drive shaft 22 extending through an opening in said wall, a PTC heating element 23, and, in this embodiment, a temperature control circuit board 24, and a temperature sensor 25. The circuit board 24 is also supported on said other face of the wall 20 and provides a control arrangement, which is designed:

(i) to provide a power supply to the PTC heating element 23, which projects from the lower wall of the housing 3 so that (with the housing fitted), it is immersed in the water of the tank 9, (ii) to provide a regulated power supply to the motor 21 so that the fan 20 passes air drawn via slit openings 26 in the rear wall 15 of the housing 3 across the water in the tank 9 to the face mask 5 via air path 13 in a volume which (as described in our co-pending Patent Specification No. 2192136) is greater than that required for inhaling, (iii) to monitor the temperature of the air being breathed by the user via the sensor 25, which comprises a probe mounted on the wall 12 of the housing 3 so as to project into the air flow path 13 close to its upper outlet end, and (iv) to control the speed of the fan 18 to adjust the temperature of the air at the sensor probe position, as appropriate, to maintain the critical temperature.

As mentioned hereinbefore, the control arrangement would also include a timer and/or alarm circuit to warn, and preferably switch-off the apparatus automatically, after a pre-set time period, e.g. 15 or 20 minutes. Also, the circuit includes an indicator light 30 to show when the power is on and which is preferably arranged to flash when the apparatus is initially switched on until a stable working condition is reached.

The PTC heating element 23 is provided with a detachable shroud 27, which generally encloses said element, but provides openings 28 near the top of the shroud (see FIGS. 1 and 2) of a suitable plastic material which can withstand the temperature conditions, e.g. The shroud ensures that the user cannot directly touch the PTC element when the housing 3 is removed from the base 2, thereby ensuring safety from burns. However, it is has been found that temperature control of the air passing to the face mask 5 is effected more efficiently with such a shroud fitted, probably in view of the fact that the water in the tank 9 below the water surface is at a significantly lower temperature, due to the insulating effect of the plastic shroud. This leads to water at the required temperature being concentrated within the shroud and across the water surface, thereby providing a reduced thermal mass.

Tests have shown that, in use, due to the inherent temperature stability of the PTC element and the further stability provided by the surrounding shroud, it is not essential to provide control means, including the sensor 25, to monitor and adjust the temperature of the air being inhaled, thus enabling significant cost savings to be achieved.

I claim:

1. A breathing apparatus of the kind having a water chamber in which a heating element is immersed in water, the temperature of the water being controlled by the heating element so that air drawn over the heated water is maintained at an outlet of the apparatus at or close to a desired humidity and temperature, the volume of the air passing through the apparatus being substantially greater than that required for breathing and being directed into a face mask, connected to the outlet, which is formed with vents through which excess moist heated air together with air exhaled by the user can pass to atmosphere, wherein an exterior casing of the apparatus is formed from a base and a mating removable housing carrying electrical components including the heating element, the base comprises a water tank and at least a substantial portion of a duct extending therefrom which defines an air path for the moist heated air to travel from the water tank to the face mask connected to a distal end of the duct, the heating element being carried by the removable housing so that, once the removable housing is matingly engaged with the base, the heating element is at least partly immersed in the water, when water is contained in the water tank, and the base, the at least substantial portion of the duct and the face mask remaining connected to one another as a single unit upon disengagment of the removable housing from the base.

2. An apparatus according to claim 1, wherein the electronic components include a fan, a fan motor and a circuit means for powering and controlling the fan, the fan motor and the heating element.

3. An apparatus according to claim 2, wherein the circuit means is provided with means of supplying power to the heating element only when the heating element is immersed in water contained by the water tank.

4. An apparatus according to claim 2, wherein the circuit means further includes a temperature sensor which projects into the column adjacent the outlet thereof and, during use, the temperature sensor monitors the temperature of the moist heated air as it flows through the column and provides an input to the circuit means which is used to control the electronic components.

5. An apparatus according to claim 2, wherein the circuit means is provided with means for providing a warning to a user after the user has used the apparatus for a predetermined period of time.

6. An apparatus according claim 2, wherein the circuit means further includes means for indicating to a user once a stable state working condition of the apparatus has been achieved.

* * * * *